United States Patent
Al-Ali et al.

(10) Patent No.: US 12,109,012 B2
(45) Date of Patent: Oct. 8, 2024

(54) PLETHYSMOGRAPH VARIABILITY PROCESSOR

(71) Applicant: Masimo Corporation, Irvine, CA (US)

(72) Inventors: Ammar Al-Ali, San Juan Capistrano, CA (US); Walter M. Weber, Laguna Hills, CA (US); Anmol B. Majmudar, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 17/647,819

(22) Filed: Jan. 12, 2022

(65) Prior Publication Data

US 2022/0240801 A1    Aug. 4, 2022

Related U.S. Application Data

(63) Continuation of application No. 16/126,523, filed on Sep. 10, 2018, now Pat. No. 11,229,374, which is a
(Continued)

(51) Int. Cl.
*A61B 5/00* (2006.01)
*A61B 5/02* (2006.01)
(Continued)

(52) U.S. Cl.
CPC ........ *A61B 5/0295* (2013.01); *A61B 5/02416* (2013.01); *A61B 5/0261* (2013.01);
(Continued)

(58) Field of Classification Search
None
See application file for complete search history.

(56) References Cited

U.S. PATENT DOCUMENTS

| 4,109,643 A | 8/1978 | Bond et al. |
| 4,432,374 A | 2/1984 | Osanai |

(Continued)

FOREIGN PATENT DOCUMENTS

| JP | 2001-321347 | 11/2001 |
| JP | 2002-028138 | 1/2002 |

(Continued)

OTHER PUBLICATIONS

US 2024/0016391 A1, 01/2024, Lapotko et al. (withdrawn)
(Continued)

*Primary Examiner* — Michael R Bloch
(74) *Attorney, Agent, or Firm* — Knobbe Martens Olson & Bear, LLP

(57) ABSTRACT

A plethysmograph variability processor inputs a plethysmograph waveform having pulses corresponding to pulsatile blood flow within a tissue site. The processor derives plethysmograph values based upon selected plethysmograph features, determines variability values, and calculates a plethysmograph variability parameter. The variability values indicate the variability of the plethysmograph features. The plethysmograph variability parameter is representative of the variability values and provides a useful indication of various physiological conditions and the efficacy of treatment for those conditions.

6 Claims, 4 Drawing Sheets

Related U.S. Application Data continuation of application No. 13/858,249, filed on Apr. 8, 2013, now Pat. No. 10,092,200, which is a continuation of application No. 11/952,940, filed on Dec. 7, 2007, now Pat. No. 8,414,499.

(60) Provisional application No. 60/998,782, filed on Oct. 12, 2007, provisional application No. 60/873,663, filed on Dec. 9, 2006.

(51) Int. Cl.
    *A61B 5/024*      (2006.01)
    *A61B 5/026*      (2006.01)
    *A61B 5/0295*      (2006.01)
    *A61B 5/1455*      (2006.01)
    *G16H 50/20*      (2018.01)

(52) U.S. Cl.
    CPC ........ *A61B 5/14551* (2013.01); *A61B 5/4848* (2013.01); *A61B 5/7278* (2013.01); *G16H 50/20* (2018.01)

(56) References Cited

U.S. PATENT DOCUMENTS

| | | |
|---|---|---|
| 4,859,056 A | 8/1989 | Prosser et al. |
| 4,867,165 A | 9/1989 | Noller et al. |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Hink et al. |
| 5,111,817 A | 5/1992 | Clark et al. |
| 5,119,814 A | 6/1992 | Minnich |
| 5,163,438 A | 11/1992 | Gordon et al. |
| 5,277,181 A | 1/1994 | Mendelson et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,490,506 A | 2/1996 | Takatani et al. |
| 5,494,043 A | 2/1996 | O'Sullivan et al. |
| 5,533,511 A | 7/1996 | Kaspari et al. |
| 5,534,851 A | 7/1996 | Russek |
| 5,553,615 A | 9/1996 | Carim et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,613,496 A | 3/1997 | Arand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,766,127 A | 6/1998 | Pologe et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,862,805 A | 1/1999 | Nitzan |
| 5,890,929 A | 4/1999 | Mills et al. |
| 5,904,654 A | 5/1999 | Wohltmann et al. |
| 5,919,134 A | 7/1999 | Diab |
| 5,934,277 A | 8/1999 | Mortz |
| 5,934,925 A | 8/1999 | Tobler et al. |
| 5,940,182 A | 8/1999 | Lepper, Jr. et al. |
| 5,984,893 A | 11/1999 | Ward |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,165,151 A | 12/2000 | Weiner |
| 6,168,568 B1 | 1/2001 | Gavriely |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,361,501 B1 | 3/2002 | Amano et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,385,471 B1 | 5/2002 | Mortz |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |

(56) References Cited

U.S. PATENT DOCUMENTS

| | | |
|---|---|---|
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,869,402 B2 | 3/2005 | Arnold |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,942,622 B1 | 9/2005 | Turcott |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,027,850 B2 | 4/2006 | Wasserman |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,917 B2 | 5/2006 | Arnold |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,201,734 B2 | 4/2007 | Hickle |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,403,806 B2 | 7/2008 | Norris |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |

(56) References Cited

U.S. PATENT DOCUMENTS

| | | |
|---|---|---|
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |

(56) References Cited

U.S. PATENT DOCUMENTS

| | | |
|---|---|---|
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |

(56) References Cited

U.S. PATENT DOCUMENTS

| | | |
|---|---|---|
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |

(56) References Cited

U.S. PATENT DOCUMENTS

| | | |
|---|---|---|
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| 11,229,374 B2 | 1/2022 | Al-Ali et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 2001/0034477 A1 | 10/2001 | Mansfield et al. |
| 2001/0039483 A1 | 11/2001 | Brand et al. |
| 2002/0002339 A1 | 1/2002 | Sugo et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0163054 A1 | 8/2003 | Dekker |
| 2003/0212312 A1 | 11/2003 | Coffin, IV et al. |
| 2004/0034293 A1 | 2/2004 | Kimball |
| 2004/0039273 A1 | 2/2004 | Terry |
| 2004/0087846 A1 | 5/2004 | Wasserman |
| 2004/0106163 A1 | 6/2004 | Workman, Jr. et al. |
| 2005/0010166 A1 | 1/2005 | Hickle |
| 2005/0027205 A1 | 2/2005 | Tarassenko et al. |
| 2005/0048456 A1 | 3/2005 | Chefd'hotel et al. |
| 2005/0055276 A1 | 3/2005 | Kiani et al. |
| 2005/0070774 A1 | 3/2005 | Addison et al. |
| 2005/0085702 A1 | 4/2005 | Diab |
| 2005/0177096 A1 | 8/2005 | Bollish et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2006/0258921 A1 | 11/2006 | Addison et al. |
| 2007/0032732 A1 | 2/2007 | Shelley et al. |
| 2007/0055198 A1 | 3/2007 | O'Mahony et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0067132 A1 | 3/2008 | Ross et al. |
| 2008/0079299 A1 | 4/2008 | Jackson |
| 2008/0094228 A1 | 4/2008 | Welch et al. |
| 2008/0103375 A1 | 5/2008 | Kiani |
| 2008/0167541 A1 | 7/2008 | Takala et al. |
| 2008/0221418 A1 | 9/2008 | Al-Ali et al. |
| 2008/0221512 A1 | 9/2008 | Da Silva et al. |
| 2008/0304580 A1 | 12/2008 | Ichiyama |
| 2009/0036759 A1 | 2/2009 | Ault et al. |

(56) References Cited

U.S. PATENT DOCUMENTS

| | | |
|---|---|---|
| 2009/0043179 A1 | 2/2009 | Melker et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2009/0312612 A1 | 12/2009 | Rantala |
| 2009/0326349 A1 | 12/2009 | McGonigle et al. |
| 2010/0004518 A1 | 1/2010 | Vo et al. |
| 2010/0014761 A1 | 1/2010 | Addison et al. |
| 2010/0016682 A1 | 1/2010 | Schluess et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2010/0298730 A1 | 11/2010 | Tarassenko et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank et al. |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |

(56) References Cited

U.S. PATENT DOCUMENTS

| | | |
|---|---|---|
| 2017/0325728 A1 | 11/2017 | Al-Ali et al. |
| 2017/0332976 A1 | 11/2017 | Al-Ali |
| 2017/0340293 A1 | 11/2017 | Al-Ali et al. |
| 2017/0360310 A1 | 12/2017 | Kiani |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192953 A1 | 7/2018 | Shreim et al. |
| 2018/0199871 A1 | 7/2018 | Pauley et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0082979 A1 | 3/2019 | Al-Ali et al. |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |

FOREIGN PATENT DOCUMENTS

| | | |
|---|---|---|
| JP | 2002-191569 | 7/2002 |
| JP | 2006-516000 | 6/2006 |
| JP | 2009-540509 | 11/2009 |
| WO | WO 2004/034898 | 4/2004 |
| WO | WO 2004/052196 | 6/2004 |
| WO | WO 2004/080300 | 9/2004 |
| WO | WO 2005/096922 | 10/2005 |

(56) References Cited

FOREIGN PATENT DOCUMENTS

| WO | WO-2005096922 A1 * | 10/2005 | ......... A61B 5/14551 |
|---|---|---|---|
| WO | WO 2006/097866 | 9/2006 | |
| WO | WO 2008/073855 | 6/2008 | |

OTHER PUBLICATIONS

Awad et al., Different Responses of Ear and Finger Pulse Oximeter Wave Form to Cold Pressor Test, Anesth Analg 2001, vol. 92, pp. 1483-1486.

Awad, et al., How Does the Plethysmogram Derived from the Pulse Oximeter Relate to Arterial Blood Pressure in Coronary Artery Bypass Graft Patients? The International Anesthesia Research Society, 2001, pp. 1466-1471.

Barach, Paul, "Pulsus Paradoxus". Hospital Physician, Jan. 2000, pp. 49-50.

Cannesson et al., New Algorithm for Automatic Estimation of the Respiratory Variations in the Pulse Oximeter Waveform in Mechanically Ventilated Patients, Crit Care Med 2007 Abstract vol. 35 No. 12 (Suppl), p. A87.

Cannesson et al., New Algorithm for Automatic Estimation of the Respiratory Variations in the Pulse Oxymeter Waveform, ASA Annual Meeting Abstracts Oct. 13, 2007.

Cannesson et al., "Relation Between Respiratory Variations in Pulse Oximetry Plethysmographic Waveform Amplitude and Arterial Pulse Pressure in Ventilated Patients", Critical Care 2005, Aug. 23, 2005, pp. R562-R568.

Cannesson et al., Respiratory variations in pulse oximeter waveform amplitude are influenced by venous return in mechanically ventilated patients under general anesthesia, European Journal of Anesthesiology 2007, vol. 24, pp. 245-251.

Cannesson et al., Respiratory Variations in Pulse Oximetry Plethysmographic Waveform Amplitude to Predict Fluid Responsiveness in the Operating Room, Anesthesiology, V 106, No. 6, Jun. 2007, pp. 1105-1111.

Cannesson, MD. "Use of the Pulse Oximeter Waveform as a Non Invasive Functional Hemodynamic Monitoring". Anaesthesia, Pain, Intensive Care and Emergency A.P.I.C.E. 2008, pp. 23-28.

Clark et al., Comparison of Traditional and Plethysmographic Methods for Measuring Pulsus Paradoxus, Jan. 2004; 158:48-51.

Steele et al., "Pulsus Paradoxus: An Objective Measure of Severity in Croup", American Journal of Respiratory and Critical Care Medicine, 1998, vol. 157, pp. 331-334.

Dell R et al, Direct Measurement of Pulsus Paradoxus in Acute Severe Asthma, Sep. 1996; 150(9):914-8.

Dorlas, J.C. and JA Nijboer (1985) "Photo-electric plethysmography as a monitoring device in anesthesia. Application and interpretation." British Journal of Anaesthesia 57 (5): 524-30.

Feissel et al., Plethysmographic dynamic indices predict fluid responsiveness in septic ventilated patients, Intensive Care Med (2007) 33, pp. 993-999.

Frey et al., Pulse Oximetry for Assessment of Pulsus Paradoxus: A Clinical Study in Children, Intensive Care Med, 1998, vol. 24, pp. 242-246.

Goparvar et al., "Evaluating the Relationship Between Arterial Blood Pressure Changes and Indices of Pulse Oximetric Plethysmography," Anesthesia-Analgesia 2002; 95:1686-1690.

International Search Report received in PCT Application No. PCT/US2007/086879, dated Aug. 13, 2008 in 11 pages.

Jablonka et al. "Ear Plethysmographic Changes during Hemodialysis," American Society of Anesthesiologist Annual Meeting (Oct. 23-27, 2004) Abstract a-588; Sep. 5, 2004.

Jay et al, Analysis of Physician Ability in the Measurement of Pulsus Paradoxus by Sphygmomanometry, 2000; 228;348-352.

James et al. "Vascular volume monitoring with pulse oximetry during pediatric anesthesia [correspondence]." Apr. 1990, Canadian Journal of Anaesthesia 37(2):266-7.

Jespersen, L. T. and O. Lederballe (1986). "Quantitative photoplethysmography." Surgery 99(1):130.

Jespersen, L.T. and O.L. Pedersen (1986). "The quantitative aspect of photoplethysmography revised." Heart Vessels 2(3): 186-90.

Keller et al., "Ability of pleth variability index to detect hemodynamic changes induced by passive leg raising in spontaneously breathing volunteers", Critical Care, Mar. 6, 2008, p. 1-7, vol. 12 No. 2.

Kim et al. (1986). "Pulse oximetry and circulatory kinetics associated with pulse volume amplitude measured by photoelectric plethysmography." Anesth Analg 65 (12): 1333-9.

Kirk Shelley M.D., Ph.D., Using the Pulse Oximeter to determine Intravascular Volume Status Non-Invasively, Yale University, School of Medicine, undated PowerPoint presentation, 17 slides.

Lherm et al. (1995). "Correlation between plethysmography curve variation (dpleth) and pulmonary capillary wedge pressure (pcwp) in mechanically ventilated patients." British Journal of Anaesthesia Suppl. 1 (74): 41.

Mooser et al., "Le pouls paradoxal" Schweiz. Rundschau Med. (Praxis) 83, Nr. 6 (1994): pp. 158-162 (with English Abstract).

Murray et al., The Peripheral Pulse Wave: Information Overlooked, Journal of Clinical Monitoring 1996, vol. 12, pp. 365-377.

Natalini et al., Arterial Versus Plethysmographic Dynamic Indices to Test Responsiveness for Testing Fluid Administration in Hypotensive Patients: A Clinical Trial, Anesth Analg Dec. 2006 vol. 103 No. 6, Paces 1478-1484.

Natalini et al., Variations in Arterial Blood Pressure and Photoplethysmography During Mechanical Ventilation, Anesth Analg Nov. 2006 vol. 103 No. 5, pp. 1182-1188.

Nolan et al., "Invasive Hemodynamic Monitoring in Obstetrics. A Critical Review of its Indications, Benefits, Complications, and Alternatives", American College of Chest Physicians 101, May 1992, p. 1429-1433.

Partridge, Brian L., MD, DPhil., Use of Pulse Oximetry as a noninvasive indicator of intravascular volume status, Journal of Clinical Monitoring 1987 vol. 3 No. 4, pp. 263-268.

Pinsky et al., "Functional hemodynamic monitoring", Critical Care, Dec. 2005, p. 566-572, vol. 9 No. 6.

Pitson et al., "Use of Pulse Transit Time as a Measure of Inspiratory Effort in Patients with Obstructive Sleep Apnea", Eur Respir J, 1995, vol. 8, pp. 1669-1674.

Pleth Variability Index: A Dynamic Measurement to Help Assess Physiology and Fluid Responsiveness, Technical Bulletin, http://www.masimo.co.uk/pdf/pvi/LAB7698A_Technical_Bulletin_Pleth_Variability_Index_British.pdf, 12 pgs., prepared Jun. 13, 2013.

Rayner et al, Continuous Noninvasive Measurement of Pulsus Paradoxus Complements Medical Decision Making in Assessment of Acute Asthma Severity, 2006; 130:754-765.

Seidl et al., "Does Red Blood Cell Transfusion Change the Near Infra Red Photoplethysmography Signal in Infants?" Intensive Care Medicine, vol. 30, No. 9, pp. 1602-1606, Aug. 2004.

Shamir et al., Pulse Oximetry Plethysmographic Waveform During Changes in Blood Volume, British Journal of Anaesthesia, 1999, vol. 82, No. 2, pp. 178-181.

Shelley et al, The Use of Joint Time Frequency Analysis to Quantify the Effect of Ventilation on the Pulse Oximeter Waveform, Journal of Clinical Monitoring and Computing (2006) 20: 81-87.

Shelley et al., What Is the Best Site for Measuring the Effect of Ventilation on the Pulse Oximeter Waveform?, Anesth Analg, Aug. 2006, vol. 103 No. 2, pp. 372-377.

Shelley, et al., Arterial—Pulse Oximetry Loops: A New Method of Monitoring Vascular Tone, Journal of Clinical Monitoring, Jul. 1997, pp. 223-228.

Shelley, et al., Pulse Oximeter Waveform: Photoelectric Plethysmography, in Clinical Monitoring, Carol Lake, R. Hines, and C. Blitt, Eds.: W.B. Saunders Company, 2001, pp. 420-428.

Steele DW et al, Continuous Noninvasive Determination of Pulsus Paradoxus: A Pilot Study, Oct. 1995;8(10):1669-74.

Shamir et al., "Plethysmographic Waveform Variation as an Indicator to Hypovolemia," Anesthesia-Analgesia 2003; 97:602-603.

Swank, Kenneth, "Trauma Fluid Resuscitation," 2003 Handout—Colorado Review of Anesthesia & Ski Holiday (CRASH), Dept. of Anesthesiology, University of Colorado School of Medicine, 2003, Version 12-02, pp. 19.

Szecsei, "Homework Helpers Basic Math and Pre-Algebra", 2006, The Career Press, p. 133.

(56) References Cited

OTHER PUBLICATIONS

Tamburro et al, Detection of Pulsus Paradoxus Associated with Large Pericardial Effusions in Pediatric Patients by Analysis of the Pulse-Oximetry Waveform, 2002; 109; 673-677.

Vincent et al., "Clinical review: Update on hemodynamic monitoring—a consensus of 16", Critical Care, Aug. 18, 2011, p. 1-8, vol. 15 No. 229.

Wright et al., "Continuous, Noninvasive Measurement of Pulsus Paradoxus in Patients with Acute Asthma", Archives of Pediatrics & Adolescent Medicine, Sep. 1996, pp. 914-918.

Yamakage et al., "Can Variation of "Pulse Amplitude Value" Measured by a Pulse Oximeter Predict Intravascular Volume?" American Society of Anesthesiologists Annual Meeting (Oct. 23-27, 2004) Abstract A-582; Sep. 5, 2004.

510(k) Summary: K053269, Masimo Corporation, Masimo SET® Rad-8 Pulse Oximeter, Model Rad-8, Kestrel, Pulse Oximeter, Dec. 21, 2005, in 8 pages.

510(k) Summary: K073024, Masimo Corporation, "Masimo Rainbow SET® Rad 87 Pulse CO-Monitor and Accessories", Pulse Oximeter, Feb. 8, 2008, in 9 pages.

510(k) Summary: K080238, Masimo Corporation, "Masimo Rainbow SET® Radical 7 CO-Oximeter", Pulse Oximeter and Sensor, May 12, 2008, in 12 pages.

510(k) Summary: K092838, Masimo Corporation, "Masimo SET® Rad-8 Pulse Oximeter and Accessories, Model Rad-8", Pulse Oximeter, Oct. 15, 2009, in 7 pages.

510(k) Summary: K091241, Masimo Corporation, "Masimo Rainbow SET® Rad 87 CO-Oximeter and Accessories", Pulse Oximeter and Sensor, Nov. 6, 2009, in 9 pages.

510(k) Summary: K120657, Masimo Corporation, "Masimo SET® Rad 5 Pulse Oximeter; Masimo SET® Rad 5v Pulse Oximeter; Masimo SET® Rad-8 Pulse Oximeter; Masimo rainbow SET® Rad 57 Pulse CO-Oximeter; Masimo rainbow SET® Radical 7 Pulse CO-Oximeter; Masimo rainbow SET® Rad 87 Pulse CO-Oximeter; Masimo LNOP Oximetry Sensors; Masimo LNCS/M-LNCS Oximetry Sensors; Masimo LNOP/M-LNCS/LNCS Multisite-L Oximetry Sensors; Masimo Lnop/M-Lncs/Lncs Y-1 Oximetry Sensors; Masimo ReSposable SPO2 Series Oximetry Sensors", Pulse Oximeter and Oximeter Sensor, Sep. 19, 2012, in 15 pages.

\* cited by examiner

PLETHYSMOGRAPH VARIABILITY PROCESSOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Pulse oximetry utilizes a noninvasive sensor to measure oxygen saturation ($SpO_2$) and pulse rate of a person. The sensor has light emitting diodes (LEDs) that transmit optical radiation of red and infrared wavelengths into a tissue site and a detector that responds to the intensity of the optical radiation after attenuation by pulsatile arterial blood flowing within the tissue site. Furthermore, the sensor may be attached to a patient's finger, foot, ear lobe, digit or other portion of the body where blood flows close to the skin. Pulse oximeters have gained rapid acceptance in a wide variety of medical applications, including surgical wards, intensive care and neonatal units, general wards, home care, physical training, and virtually all type of monitoring scenarios.

Pulse oximeters capable of reading through motion induced noise are disclosed in at least U.S. Pat. Nos. 6,770,028, 6,658,276, 6,584,336, 6,263,222, 6,157,850, 5,769,785, and 5,632,272, which are assigned to Masimo Corporation ("Masimo") of Irvine, California and are incorporated by reference herein. Low noise pulse oximetry sensors are disclosed in one or more of U.S. Pat. Nos. 7,027,849, 6,985,764, 6,934,570 6,760,607 6,377,829 6,285,896 5,782,757 5,638,818, which are also assigned to Masimo and incorporated by reference herein. Moreover, pulse oximeters capable of reading through motion induced noise and low noise optical sensors including LNOP® disposable, reusable and/or multi-site sensors and Radical®, Rad-5™, Rad-8™, Rad-9™, PPO+™ monitors are also available from Masimo.

Multiple parameter monitors and multiple wavelength sensors are described in U.S. patent application Ser. No. 11/367,033 entitled Noninvasive Multiple Parameter Patient Monitor filed Mar. 1, 2006 and U.S. patent application Ser. No. 11/367,013 entitled Multiple Wavelength Sensor Emitters filed Mar. 1, 2006, incorporated by reference herein. Moreover, multiple parameter monitors and multiple wavelength sensors including Rad57™ and Radical-7™ monitors and Rainbow™ Rainbow™-brand adhesive and reusable sensors are available from Masimo. MS-brand processor boards incorporating SHARC® DSPs from Analog Devices, Inc. are also available from Masimo.

SUMMARY

An aspect of a plethysmograph variability processor inputs a plethysmograph waveform, derives perfusion values, determines variability values, and calculates a plethysmograph (pleth) variability index. The plethysmograph waveform has pulses corresponding to pulsatile blood flow within a tissue site. The perfusion values correspond to the pulses. The variability values are each indicative of the variability of a series of the perfusion values. The plethysmograph variability index is representative of the variability values. The plethysmograph variability index is displayed.

In various embodiments, the perfusion values are derived by identifying peaks and valleys for the pulses, calculating AC values for the pulses from the peaks and the valleys, calculating DC values for the pulses, and normalizing the AC values with the DC values. Variability values are determined by accumulating the perfusion values in buffers and calculating one of the variability values for each of the buffers. As an example, variability values are determined by sorting the perfusion values within each of the buffers from the largest of the perfusion values to the smallest of the perfusion values and trimming at least one of the largest perfusion values and at least one of the smallest perfusion values from each of the buffers.

Plethysmograph variability indexes (PVIs) are determined from a percentage difference between a maximum perfusion value and a minimum perfusion value for each of the buffers. A median value of the PVIs is calculated. In an embodiment, physiologically acceptable pulses are identified and a minimum amount of time's worth of acceptable data for each buffer is determined. An IR channel is input for the plethysmograph waveform and a red channel is used to verify acceptable pulses.

An aspect of a plethysmograph variability processing system is an optical sensor that transmits multiple wavelengths of optical radiation into a tissue site, detects the optical radiation after attenuation by pulsatile blood flowing within the tissue site, and generates a sensor signal responsive to the detected optical radiation. A patient monitor demodulates the sensor signal so as to generate a plethysmograph channels. A digital signal processor (DSP) within the patient monitor inputs at least one of the plethysmograph channels and outputs a plethysmograph variability (PV) parameter accordingly. A PV process executes on the DSP so as to process the plethysmograph channel and derive the PV parameter. A patient monitor output is responsive to the PV parameter.

In various embodiments, the PV process has a plethysmograph input corresponding to the at least one plethysmograph channel. The pleth has pleth features. A measure pleth process extracts the pleth values from the plethysmograph according to the pleth features. A pleth value input corresponds to the pleth values. A pleth variability process generates a plurality of variability values from the pleth values. A pleth variability input corresponds to the variability values. A variability parameter process generates a pleth variability (PV) parameter from the variability values. Physiological acceptability criteria are applied to the plethysmograph input. A reduce data dispersion process trims outlying ones of the pleth values according to dispersion criteria. Post processing applies at least one of a smoothing or slew rate limit to the PV parameter. Pre-processing applies a bandpass filter to the plethysmograph input so as to remove a cyclical baseline shift or oscillation from the plethysmograph. The patient monitor output generates a graph of the PV parameter versus time so as to indicate a trend in plethysmograph variability.

An aspect of a plethysmograph variability method inputs plethysmograph channels, measures pleth values from the input and defines windows each encompassing a unique time interval of the plethysmograph values. Variability values are calculated, where each of the variability values are derived from the plethysmograph values encompassed in a unique one of the windows. Second windows are defined, each encompassing a unique time interval of the variability values. Parameter values are calculated, where each of the parameter values are derived from the variability values encompassed in a unique one of the second windows.

Parameter values are output. In various embodiments, the plethysmograph channels each have pulses corresponding to pulsatile blood flow within a tissue site, and the plethysmograph values are based upon the pulses. The plethysmograph values are measures of blood perfusion at the tissue site. In alternative embodiments, plethysmograph values are based upon area under absorption pulses, an envelope of the pulses, a time series of normalized envelope heights or a time series of normalized envelope areas.

An aspect of a plethysmograph variability processing system has a sensor that transmits multiple wavelengths of optical radiation into a tissue site and that detects the optical radiation after attenuation by pulsatile blood flow within a tissue site so as to provide a plethysmograph input to a digital signal processor (DSP). The input is selected from channels corresponding to the multiple wavelengths. The DSP executes instructions for deriving plethysmograph variability from the plethysmograph. A measuring means generates plethysmograph values from the plethysmograph input according to predefined plethysmograph features. A calculation means derives variability values from the plethysmograph values, and a reduction means deriving a plethysmograph variability (PV) parameter from the plethysmograph values. In various embodiments, a first accumulation means applies a variability formula to a window of plethysmograph values. A dispersion reduction means trims outlying values from the first accumulation means. A second accumulation means applies data reduction criteria to a window of variability values. An acceptance means eliminates pulses from the plethysmograph input that are not physiologically acceptable. A post-processing means limits the slope of the PV parameter.

DETAILED DESCRIPTION

PV Monitor

Figure 1:
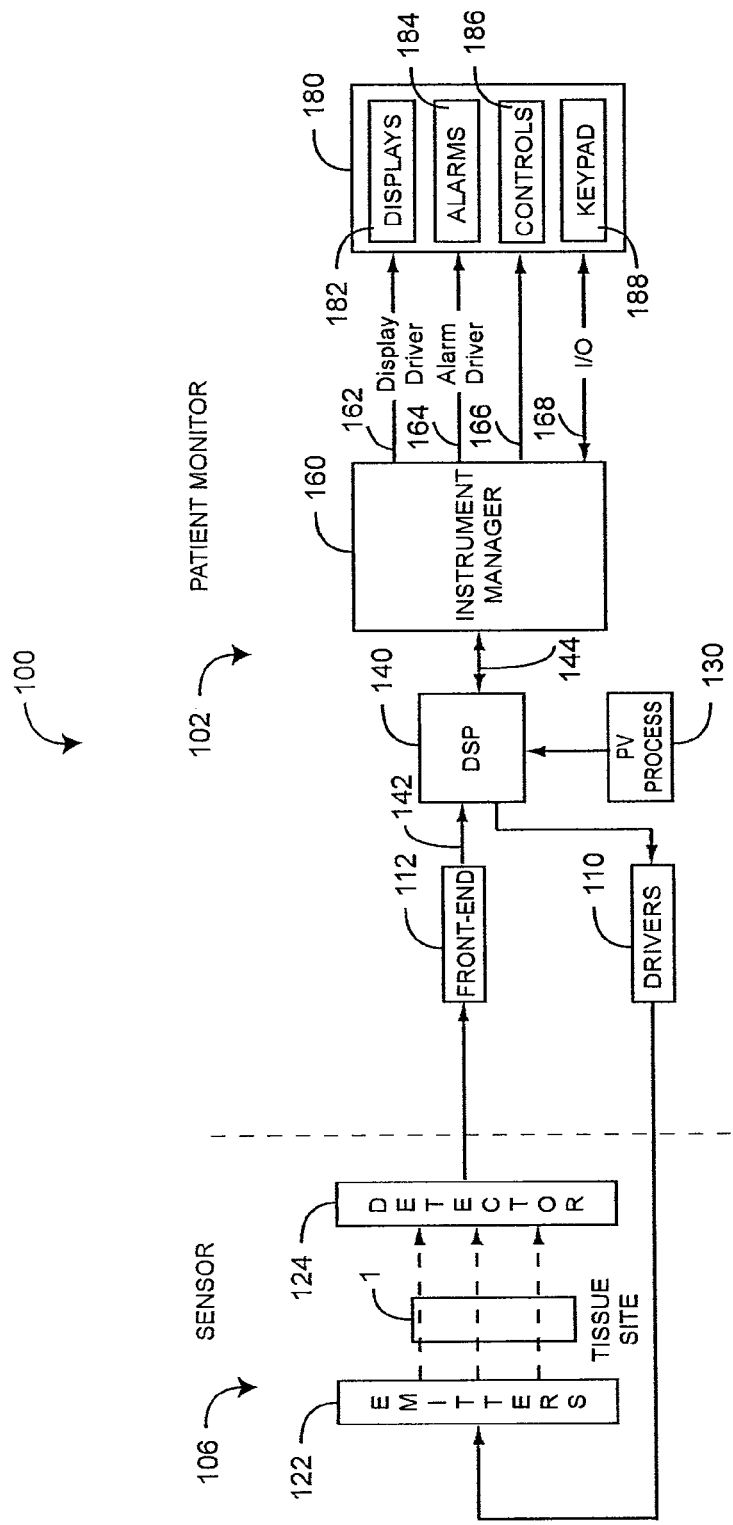
FIG. 1 is a general block diagram of a plethysmograph variability processing system.

FIG. 1 illustrates a plethysmograph variability processing system 100 embodiment, which calculates one or more measures of plethysmograph variability (PV). The plethysmograph variability processing system 100 advantageously provides at least some of displays, alarms or controls responsive to PV so as to indicate, and affect the treatment of, a patient condition. The PV processing system 100 may further generate $SpO_2$, pulse rate (PR), perfusion index (PI), signal quality and in multiple wavelength configurations additional blood parameter measurements such as HbCO and HbMet.

As shown in FIG. 1, the PV processing system 100 has a patient monitor 102 and a sensor 106. The sensor 106 attaches to a tissue site 1 and includes a plurality of emitters 122 capable of irradiating the tissue site 1 with at least two wavelengths of light, such as the red and infrared (IR) wavelengths utilized in pulse oximeters and in some configurations multiple wavelengths different than or in addition to those red and IR wavelengths. The sensor 106 also includes one or more detectors 124 capable of detecting the light after attenuation by the tissue 1.

Also shown in FIG. 1, the patient monitor 102 communicates with the sensor 106 to receive one or more intensity signals indicative of one or more physiological parameters and displays the parameter values. Drivers 110 convert digital control signals into analog drive signals capable of driving sensor emitters 122. A front-end 112 converts composite analog intensity signal(s) from light sensitive detector (s) 124 into digital data 142 input to the DSP 140. The input digital data 142 is referred to herein as a plethysmograph waveform, plethysmograph or pleth for short. The digital data 142 has plethysmograph channels corresponding to each emitter wavelength, such as a red channel and an IR channel. The digital data 142 is representative of a change in the absorption of particular wavelengths of light as a function of the changes in body tissue resulting from pulsing blood. The DSP 140 may comprise a wide variety of data and/or signal processors capable of executing programs for determining physiological parameters from input data. In an embodiment, the DSP executes one or more pleth variability (PV) processes 130, such as described with respect to FIGS. 3-4, below. In an embodiment, the PV processes 130 may be implemented in software, firmware or other form of code or instructions, or logic or other hardware, or a combination of the above.

Further shown in FIG. 1, the instrument manager 160 may comprise one or more microcontrollers controlling system management, such as monitoring the activity of the DSP 140. One or more output devices 180 include displays 182, alarms 184 and controls 186. Displays 182 may be numerical, such as readouts, or graphical, such as trends and bar graphs, generated by LEDs, LCDs or CRTs to name a few. Displays 182 may also be indicators, such as LEDs of various colors that signify variability magnitude. Alarms 184 may be visual or audible indications that variability is, say, above a predetermined threshold. Controls 186 may be inputs to medical equipment, such as drug administration devices, ventilators and fluid Ws, so as to control the amount of administered drugs, ventilator settings or the amount of infused fluids based up pleth variability. The instrument manager 160 also has an input/output (I/O) port 168 that provides a user and/or device interface for communicating with the monitor 102. User input devices 188 may include a keypad, touch screen, pointing device, voice recognition device, network and computer, to name a few. In an embodiment, the I/O port 168 provides initialization settings for PV processes, as described below. The monitor 102 may also be capable of storing or displaying historical or trending data related to PV and other measured parameters or combinations of measured parameters.

Pleth Waveform

Figure 2:
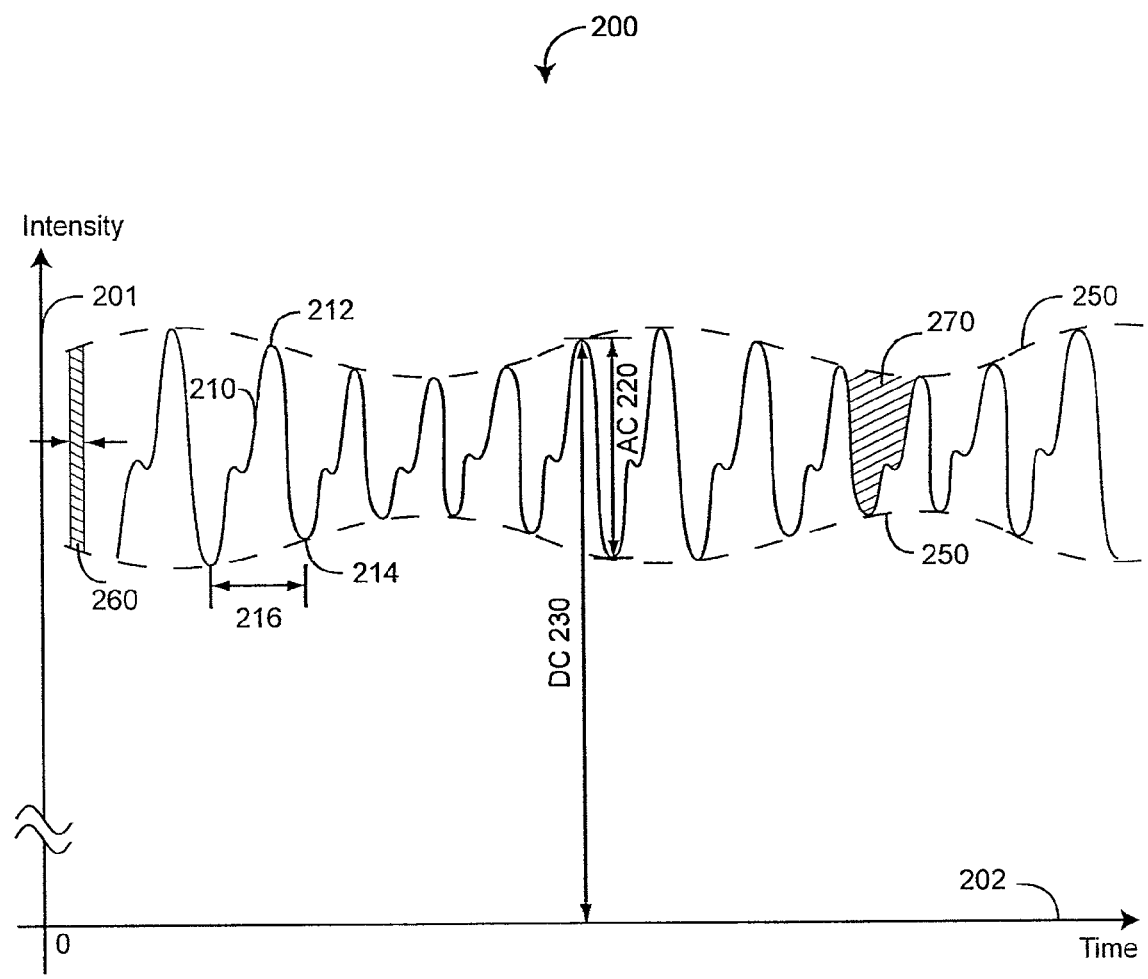
FIG. 2 is a graph of an exemplar plethysmograph.

FIG. 2 illustrates a plethysmograph 200 plotted on an intensity axis 201 versus a time axis 202. The plethysmograph 200 has multiple pulses 210 each with a peak 212 and a valley 214 and extending over a time period 216. A perfusion index (PI) value can be defined for each pulse 210:

$$PI = \frac{AC}{DC} \quad (1)$$

"AC" 220 designates a peak amplitude 212 minus a valley amplitude 214 for a particular pulse. "DC" 230 designates a peak amplitude 212 for a particular pulse. A plethysmograph variability measure is calculated that is responsive to the magnitude of pleth variations, such as depicted by envelope 250. One variability measure is a plethysmograph variability index (PVI), described with respect to FIG. 3, below. Other plethysmograph variability (PV) measures are described with respect to FIG. 4, below. Advantageously, PV measures may provide a numerical indication of a person's physical condition or health.

Pleth Variability Index (PVI)

Figure 3:
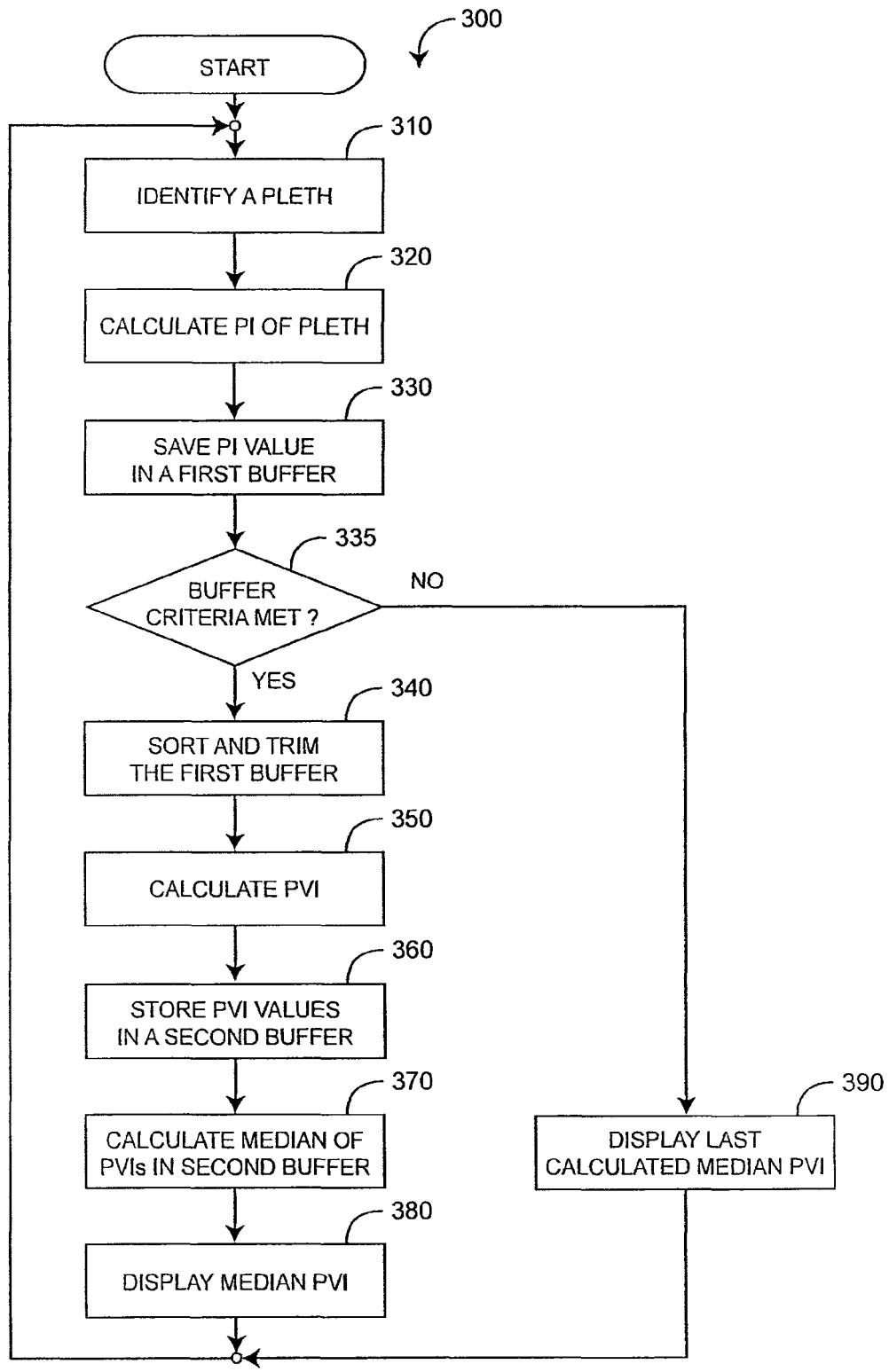
FIG. 3 is a detailed flow chart of a plethysmograph variability index process.

FIG. 3 illustrates a PVI process 300 embodiment, which derives and displays a plethysmograph variability index (PVI). Initially, a first buffer is filled with calculated perfusion index (PI) values 310-330. In an embodiment, these values are based upon the IR channel, as described above. If a sufficient amount of physiologically acceptable data is in the first buffer 335, then a second buffer is filled with calculated plethysmograph variability index (PVI) values 340-360. The median PVI in the second buffer is calculated and displayed 370-380. If the amount of acceptable data in the first buffer is insufficient, then the display is frozen with the last calculated median PVI 390.

As shown in FIG. 3, a plethysmograph is first identified 310. In particular, only physiologically acceptable pulses are used for calculating PI. Physiological plethysmograph identification is disclosed in U.S. Pat. No. 7,044,918 entitled Plethysmograph Pulse Recognition Processor, which is assigned to Masimo and incorporated by reference herein. In an embodiment, the red channel plethysmograph is utilized to verify acceptable pulses in the IR channel. The PI of each acceptable plethysmograph is then calculated 320 according to EQ. 1 and as described with respect to FIG. 2, above. The calculated PIs are stored in a first buffer 330, and the buffer criteria are tested 335. The buffer criteria require both a minimum number of acceptable pulses and a minimum amount of time of acceptable data in the first buffer.

In an embodiment, a plethysmograph 200 (FIG. 2) has a 62.5 Hz sample rate, i.e. a sample interval of 16 msec. The first buffer holds 15 sec. of data at that sample rate. Accordingly, a sliding 15 sec. window of plethysmograph data is stored in the first buffer, and the window is moved in 1.2 sec. increments. The minimum number of acceptable pulses in the first buffer is 6, and the minimum amount of acceptable data in the first buffer is 7.5 sec. The 15 sec. window size allows one respiration cycle, assuming a worse case respiration rate of 4 breaths per min. This window size also allows 6 PIs assuming a worse case pulse rate of 25 bpm. Partial plethysmograph cycles cutoff by a particular window are ignored by that window, but are taken into account in the next window.

Also shown in FIG. 3, if the buffer criteria are met 335, then the first buffer is sorted and trimmed 340. The sort orders the PI values from the minimum PI at one end of the buffer to the maximum PI at the other end of the buffer. Then a predetermined number of PIs are dropped from each end of the buffer, i.e. both the maximum PIs and the minimum PIs are deleted. In an embodiment, 12% of the PIs are trimmed from each end of the buffer. For example, if the buffer holds 10 PIs, a 12% trim=floor(10.12/100)=floor(1.2) =1, where the floor operator truncates digits to the right of the decimal point. Hence, in this example, one max PI and one min PI are dropped from the first buffer. A plethysmograph variability index (PVI) is then calculated 350 from the trimmed first buffer. In an embodiment, PVI is calculated as:

$$PVI = \frac{PI_{MAX} - PI_{MIN}}{PI_{MAX}} \times 100 \qquad (2)$$

That is, PVI is the PI variation, expressed as a percentage of the maximum PI, reflected by the PI values remaining in the first buffer.

Further shown in FIG. 3, calculated PVIs are stored in a second buffer 360. In an embodiment, the second buffer holds 11 PVIs, where one PVI is derived for every 1.2 sec shift in the sliding 15 sec. window described above. Next, the median PVI is calculated from the second buffer. This median PVI value is communicated to a display 380. If the buffer criteria 335, described above, are not met, then the last calculated median PVI value is displayed 390. That is, the display is frozen with that last calculated median PVI value until the buffer criteria are satisfied.

In an embodiment, the median PVI value is displayed as a two-digit numerical value on a monitor screen along with other parameters, such as $SpO_2$ and pulse rate. In an embodiment, the median PVI value is displayed on a monitor screen as vertical or horizontal bar graph. In an embodiment, the median PVI value is displayed on a monitor screen as trend graph versus time. In an embodiment, the median PVI value is compared to a predetermined maximum PVI threshold. If the median PVI value crosses the predetermined threshold, one or more visual or audible alarms are triggered. In an embodiment, a visual PVI alarm is one or more colored indicators, such as green, yellow and red, indicating levels of patient health or physiological condition.

Plethysmograph Variability (PV)

Figure 4:
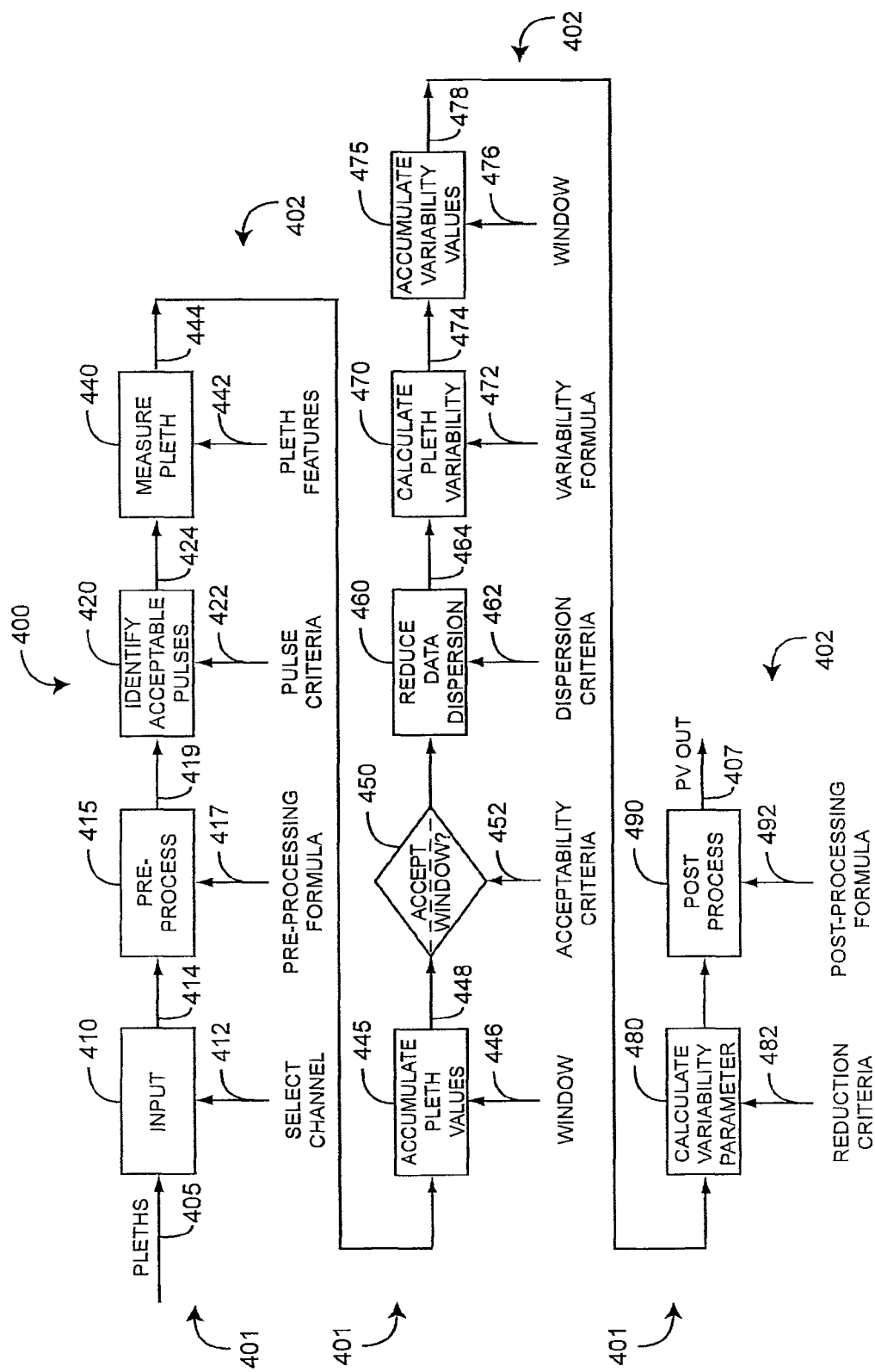
FIG. 4 is a general functional flow diagram of a plethysmograph variability process.

FIG. 4 illustrates a plethysmograph variability (PV) processor 400 embodiment having process steps 401 and initializations 402. The initializations 402 determine the specific characteristics of the process steps 401. The PV processor 400 inputs one or more plethysmograph (pleth) channels 405 and generates PV outputs 407. The pleth channels 405 each correspond to a different optical sensor wavelength, such as a red wavelength channel and an IR wavelength channel corresponding to red and IR emitters of a pulse oximeter sensor. There may be more than two channels when using a multiple wavelength sensor, such as described in U.S. patent application Ser. No. 11/367,013, cited above. For example, there may be eight channels varying in wavelength from about 630 nm to about 905 nm. In an embodiment, two or more pleth channels 405 are processed in parallel or combined as a composite pleth for increased accuracy or robustness in PV calculations. Input 410 determines which pleth channel 405 is used as the pleth input 414 for PV calculations, according to a select channel initialization 412. Input 410 may select any single channel 405 or some combination of channels 405. Pre-process 415 modifies the pleth input 414 according to a predetermined formula 417. In an embodiment, pre-process 415 filters the pleth input 414 so as to remove any slow variation or low frequency oscillation in the plethysmograph baseline or average value, such as a respiration-induced variation that shifts the entire plethysmograph up and down with inhalation and exhalation. In an embodiment, pre-process 415 is a bandpass filter having a 30 to 550 beats per minute passband. Identify acceptable pulses 420 applies pulse criteria 422 to pass only physiologically acceptable pulses 424, such as disclosed in U.S. Pat. No. 7,044,918 cited above.

As shown in FIG. 4, measure pleth 440 extracts pleth values 444 from the remaining pulses 424 according to pleth features 442. The pleth features 434 may be a pulse peak 212 (FIG. 2) and pulse valley 214 (FIG. 2) and the pleth values 444 may relate to perfusion, such as PI described with respect to EQ. 1 above. In another embodiment, the "DC" value in EQ. 1 may be other than a pulse peak, such as a pulse valley or an average of pulse peak and pulse valley, to name a few. In other embodiments, pleth features 442 may include more than two values per pulse and pleth values 444 may be other than perfusion related. Also, measure pleth 440 may be performed over more than one pulse per pleth value 444.

As shown in FIGS. 2 and 4, in an embodiment, pleth features 442 define a pleth envelope 250 interpolated from pulse peaks 212 and pulse valleys 214. Measure pleth 440 defines a series of adjacent slices 260 of envelope height and Δ width, where A may vary from one pleth sample to many samples. Accordingly, pleth values 444 are the areas of each slice. In another embodiment, measure pleth 440 calculates the area under each absorption pleth pulse 270, the absorption pleth being the inverse of the intensity pleth 200. In an embodiment, the slices 260 or areas 270 are normalized with respect to a pleth value, such as a DC value or an average value, to name a few.

Also shown in FIG. 4, accumulate pleth values 445 identifies those pleth values 444 within a specified window 446. Accept window 450 determines whether there are a sufficient number of pleth values within the window 446. If not, the remaining steps 460-490 are bypassed and a default PV output 407 is generated. If so, the remaining steps 460-490 are performed. Reduce data dispersion 460 eliminates outlying data, leaving trimmed pleth values 464, according to a dispersion criteria 462. Calculate pleth variability 470 determines a variability value 474 from the trimmed pleth values 464 according to a variability formula 472. In an embodiment, the variability formula is the percentage variability in a window compared with a maximum value in the window, such as described with respect to EQ. 2, above. Accumulate variability values 475 identifies those variability values 474 within a specified window 476. Windows 446, 476 are sliding time intervals or segments having predetermined sizes according to an initialization 402. Adjacent windows may be spaced apart, abutting or overlapping in time.

Further shown in FIG. 4, calculate variability parameter 480 determines a pleth variability (PV) parameter 407 from the accumulated variability values 478 according to a reduction criteria 482. In an embodiment, PV 407 is a median of the variability values 478 in the window 476. In other embodiments, PV 407 is any of average, mode, geometric mean or weighted mean of the windowed variability values, to name a few. Post processing on the PV parameter 407 data may be performed including smoothing and a slew rate filter. In an embodiment, an exponential smoothing is used. The slew rate filter limits the positive or negative slope of the PV parameter 407 to a predetermined maximum.

PV Applications

Many clinicians currently observe a pulse oximeter plethysmograph waveform for changes in patient physiology. Unfortunately, there is no consistency among pulse oximeter manufacturers in the way a plethysmograph waveform is displayed. Further, smoothing, autoscaling and other display data processing mask changes in the raw plethysmograph waveform. Thus, some patient physiology cannot be readily predicted from mere observation of a bedside monitor plethysmograph display. Pleth variability (PV) parameters, such as PVI, advantageously quantify plethysmograph waveform variations, which are displayed in a numerical format that can also be trended as needed. Accordingly, even slight changes in physiology may be reliably observed.

PV can be advantageously used for noninvasive functional hemodynamic monitoring. A plethysmograph waveform is responsive to beat-to-beat changes in peripheral blood volume and perfusion. Thus, plethysmograph variability reflects changes in the intravascular volume status of patients. PV parameters, as described above, are clinically useful hemodynamic measurements that respond to changes in, for example, volemia, fluid responsiveness and ventricular preload. Volemia relates to the volume of blood circulating throughout the body, which is difficult to estimate in a clinical setting. Hypovolemia, for example, is an abnormally low blood volume. Fluid responsiveness is the percent increase in ventricular stroke volume after fluid volume expansion. Ventricular preload is the degree of tension in the cardiac muscle when it begins to contract.

In particularly advantageous embodiments, a PV parameter is monitored during patient treatments. As an example, a downward trend in PV monitored during the addition of fluids to a suspected hypovolemic patient indicates the efficacy of that treatment. Likewise, a downward trend in PV monitored during administration of drugs for asthma indicates the efficacy of the administered drug and the likelihood that the asthma can be controlled.

PVI or other pulse variability (PV) measure may be a significant parameter in a variety of critical conditions, for example those conditions shown in Table 1, below.

TABLE 1

| Conditions Associated with Increased PV | |
|---|---|
| Cardiac Causes | Non-Cardiac Causes |
| Cardiogenic Shock | Hypovolemia |
| Cardiac Tamponade | Septic Shock |
| Pericardial Effusion | Anaphylactic Shock |
| Constrictive Pericarditis | Superior Vena Cava Obstruction |
| Restrictive Cardiomyopathy | Asthma |
| Acute myocardial infarction | |

A plethysmograph variability processor has been disclosed in detail in connection with various embodiments. These embodiments are disclosed by way of examples only and are not to limit the scope of the claims that follow. One of ordinary skill in art will appreciate many variations and modifications.

What is claimed is:

1. A computerized plethysmograph variability method using a signal processor comprising:
    receiving a data signal from a physiological sensor coupled to a patient;
    generating a plethysmograph waveform based at least in part on the data signal, wherein the plethysmograph waveform comprises a plurality of pulses corresponding to pulsatile blood flow within tissue of the patient;
    accumulating, in a first buffer, a plurality of perfusion values corresponding to the plurality of pulses, the plurality of perfusion values derived based on the plurality of pulses;
    determining if a sufficient amount of physiologically acceptable data is in the first buffer based at least on a length of a respiration cycle of the patient, wherein the signal processor is configured to perform specific operations when there is sufficient amount of data and when there is insufficient amount of data in the first buffer over time;

in response to determining that sufficient amount of data is in the first buffer for a specific period of time:
  determining a plurality of variability values each indicative of variability of a series of the plurality of perfusion values;
  calculating a plethysmograph variability index representative of the plurality of variability values; and
  displaying the calculated plethysmograph variability index; and
in response to determining that insufficient amount of data is in the first buffer for the specific period of time:
  displaying a previously calculated plethysmograph variability index stored in the signal processor.

2. The computerized plethysmograph variability method according to claim 1, wherein
  determining the plurality of variability values further comprises:
  sorting the plurality of perfusion values within the first buffer from a largest perfusion value to a smallest perfusion value; and
  trimming at least one perfusion value from a set of largest perfusion values and at least one perfusion value from a set of smallest perfusion values from the first buffer.

3. The computerized plethysmograph variability method according to claim 2, wherein determining the plurality of variability values further comprises calculating a plurality of plethysmograph variability indexes (PVIs) from a percentage difference between a maximum perfusion value and a minimum perfusion value for the first buffer.

4. The computerized plethysmograph variability method according to claim 3, wherein calculating qathe plethysmograph variability index comprises calculating a median value of the PVIs.

5. The computerized plethysmograph variability method according to claim 4, wherein determining if sufficient amount of physiologically acceptable data is in the first buffer comprises:
  identifying the plurality of pulses, wherein the plurality of pulses comprise physiologically acceptable pulses identified from a group comprising the physiologically acceptable pulses and physiologically unacceptable pulses; and
  determining a minimum amount of time of acceptable data in the first buffer.

6. The computerized plethysmograph variability method according to claim 5, further comprising:
  verifying the physiologically acceptable pulses using a red channel,
  wherein inputting the plethysmograph waveform comprises using an IR channel for the plethysmograph waveform.

* * * * *

UNITED STATES PATENT AND TRADEMARK OFFICE
CERTIFICATE OF CORRECTION

PATENT NO. : 12,109,012 B2
APPLICATION NO. : 17/647819
DATED : October 8, 2024
INVENTOR(S) : Ammar Al-Ali It is certified that error appears in the above-identified patent and that said Letters Patent is hereby corrected as shown below:

On the Title Page

In item (56) Other Publications, under Column no. 2, Page 10, Line no. 23, replace "No. 6, Paces 1478" with --No. 6, Pages 1478--.

In the Specification

Under Column no. 3, Line no. 21, replace "means derives variability" with --means deriving variability--.

Under Column no. 3, Line no. 25, replace "means applies a variability" with --means applying a variability--.

Under Column no. 3, Line no. 28, replace "means applies data" with --means applying data--.

Under Column no. 3, Line no. 30, replace "means eliminates pulses" with --means eliminating pulses--.

Under Column no. 4, Line no. 37, replace "fluid Ws, so" with --fluid IVs, so--.

In the Claims

Under Column no. 10, Claim 4, Line no. 5, replace "calculating qathe plethysmograph" with --calculating the plethysmograph--.

Signed and Sealed this
Seventeenth Day of December, 2024

Derrick Brent
*Acting Director of the United States Patent and Trademark Office*